(12) United States Patent
Takesako et al.

(10) Patent No.: US 6,261,826 B1
(45) Date of Patent: Jul. 17, 2001

(54) ANTIBIOTIC TKR2648 AND PROCESS FOR PRODUCING THE SAME

(75) Inventors: Kazutoh Takesako, Otsu; Hideharu Saito, Kusatsu; Mitsuhiro Ueno, Kusatsu; Naoyuki Awazu, Kusatsu; Ikunoshin Kato, Uji, all of (JP)

(73) Assignee: Takara Shuzo Co., Ltd., Kyoto (JP)

( * ) Notice: Subject to any disclaimer, the term of this patent is extended or adjusted under 35 U.S.C. 154(b) by 0 days.

(21) Appl. No.: 09/269,437
(22) PCT Filed: Oct. 31, 1997
(86) PCT No.: PCT/JP97/03998
  § 371 Date: Mar. 26, 1999
  § 102(e) Date: Mar. 26, 1999
(87) PCT Pub. No.: WO98/21196
  PCT Pub. Date: May 22, 1998

(30) Foreign Application Priority Data

Nov. 8, 1996 (JP) ................................. 8-311236

(51) Int. Cl.$^7$ ............................ C12N 1/14; C07D 309/30
(52) U.S. Cl. ................... 435/254.1; 549/292; 435/125; 435/123
(58) Field of Search ................. 435/125, 123, 435/254.1; 549/273, 292

(56) References Cited

U.S. PATENT DOCUMENTS 3,954,972  5/1976  Michel et al. .
4,668,627  5/1987  Ohsugi et al. .

FOREIGN PATENT DOCUMENTS 59-017989  1/1984  (JP) .

OTHER PUBLICATIONS

Ellestad et al., J. Org. Chem., 37:2045–2047, 1972.*
J. Chem. Soc. Perkin trans. (1981) vol. 1, No. 4 pp. 1173–1179; The Carbon–13 Nuclear Magnetic Resonance Spectra of Tetronate and 2–Pyrone Derivatives; Andrew Pelter et al.

* cited by examiner

*Primary Examiner*—Irene Marx
(74) *Attorney, Agent, or Firm*—Rhodes & Mason, PLLC

(57) ABSTRACT

Antibitic TKR2648 having the following chemical formula (I) or its pharmacologically acceptable salt.

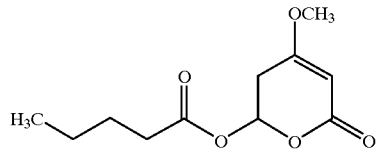

(I)

3 Claims, 5 Drawing Sheets

ANTIBIOTIC TKR2648 AND PROCESS FOR PRODUCING THE SAME

TECHNICAL FIELD

The present invention relates to TKR2648, which is an antibiotic of use as a therapeutic agent for fungal infectious diseases, a method for their production, and microorganisms producing said antibiotic.

BACKGROUND ART

Fungi are known to cause a variety of infectious diseases in man, animals, and plants. In man, for instance, they cause superficial mycosis affecting the skin, oral cavity, etc. and systemic mycosis affecting the viscera, brain, etc. They cause similar infections in pet and domestic animals as well. Furthermore, fungi inflict various hazardous effects on plants such as orchard trees and vegetables.

As the principal pathogenic fungi causing systemic mycosis in man, those of the genera Candida, Cryptococcus, and Aspergillus, among others, are known. As to superficial mycosis, Candida species affecting the skin, oral cavity, and vagina and trichophytons infecting the skin of the extremities are regarded as the major pathogenic fungi. Besides those fungi, many other fungi exist in the environment and are suspected to contaminate the animal and vegetable kingdoms.

PROBLEMS TO BE SOLVED BY THE INVENTION

As antimycotics of use for the prevention and treatment of such fungal infections and contaminations, only a very few are known. As therapeutic drugs for systemic mycosis in man and animals, for instance, amphotericin B, flucytosine, miconazole, and fluconazole can be mentioned. However, those compounds are not fully satisfactory in potency, toxic potential, or antifungal spectrum, thus being not impeccable as therapeutic drugs.

In view of the above-mentioned prior art, the present invention has for its object to provide a novel antibiotic which is of value as a therapeutic agent for fungal infections.

MEANS FOR SOLVING THE PROBLEMS

In their search for a novel antibiotic, the inventors of the present invention isolated a large number of microorganisms from the natural kingdom, isolated the antibiotics they produced, and scrutinized their biological properties. As a result, they discovered that the culture broth of a strain of microorganism of the genus Penicillium contained an antibiotic having antifungal activity against pathogenic fungi inclusive of *Candida albicans, Cryptococcus neoformans,* and *Asperaillus fumigatus.* Accordingly the inventors isolated this antibiotic and studied its physicochemical properties. As a result, they discovered that the above antibiotic is a novel substance having distinct physicochemical characteristics and named it TKR2648.

The present invention, therefore, is directed, in the first aspect, to the novel antibiotic TKR2648 which is represented by the following chemical formula (I) or its pharmacologically acceptable salt.

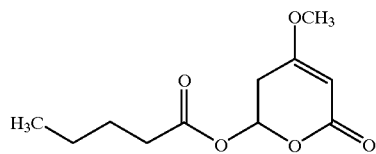

(I)

The present invention is further directed, in the second aspect, to a method of producing the novel antibiotic TKR2648 which comprises culturing a strain of microorganism belonging to the genus Penicillium and capable of elaborating said antibiotic TKR2648 and isolating said substance from the resulting culture broth.

In the third aspect, the present invention is directed to a microorganism belonging to the genus Penicillium and capable of producing the antibiotic TKR2648.

DETAILED DESCRIPTION OF THE INVENTION

The present invention is now described in detail.

The antibiotic TKR2648 of the invention has the following physicochemical characteristics (1), (2), (3), (4), (5) and (6).

(1) Mass spectrum (FAB-MS): m/z 229 [M+H]$^+$ (2) Molecular formula: $C_{11}H_{16}O_5$. High-resolution FAB-MS: 229.1090 [M+H]$^+$ (calculated value 229.1076)

(3) Specific optical rotation $[\alpha]_D^{20}$ +126° (c 1.0, methanol)

Figure 1:
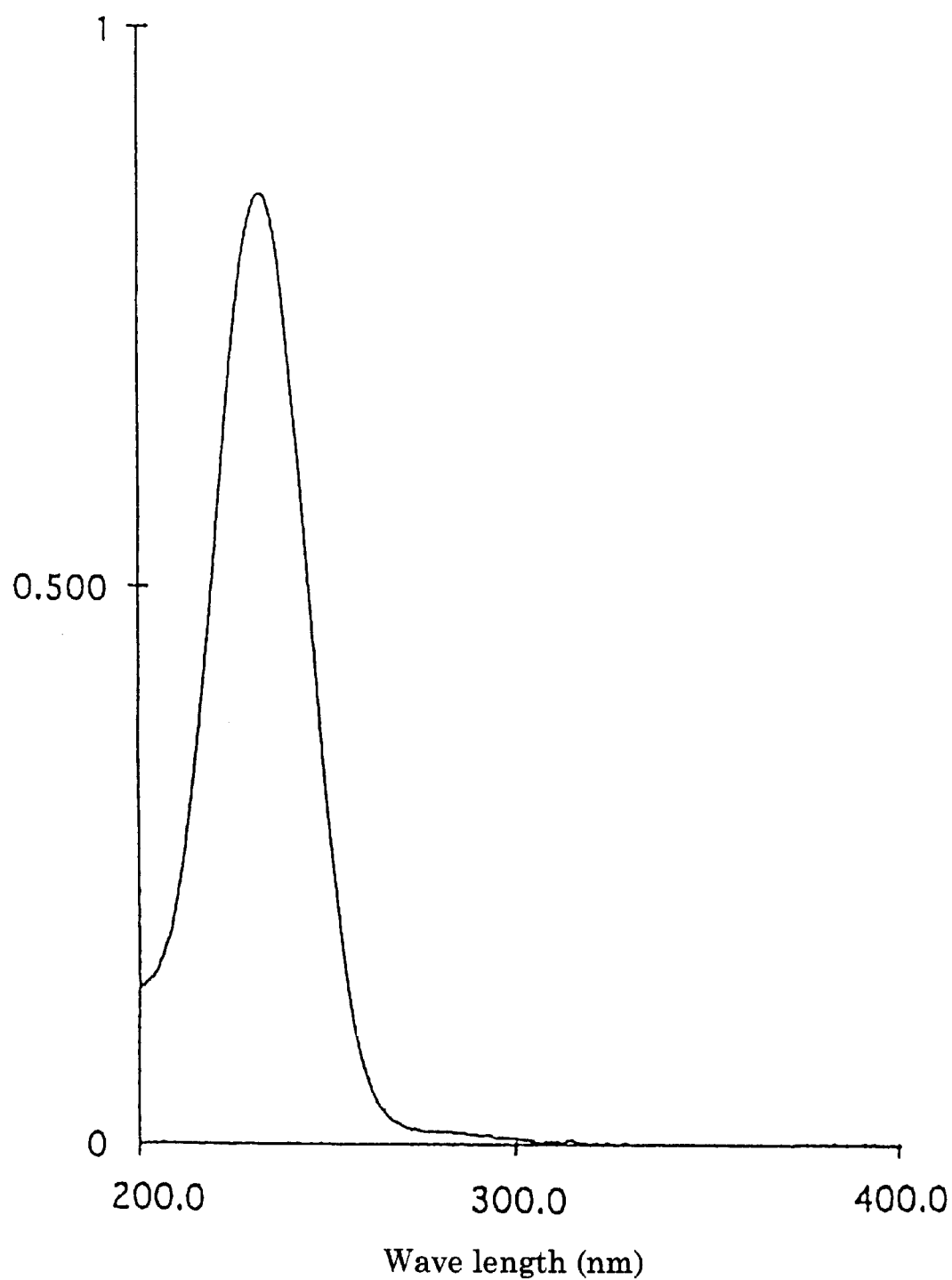
FIG. 1 is a chart showing the ultraviolet absorption spectrum of the antibiotic TKR2648.

(4) UV spectrum (in methanol): the number of wave length (nm) of maximum absorption is 232 ($E_{1cm}^{1\%}$ 510) as shown in FIG. 1.

Figure 2:
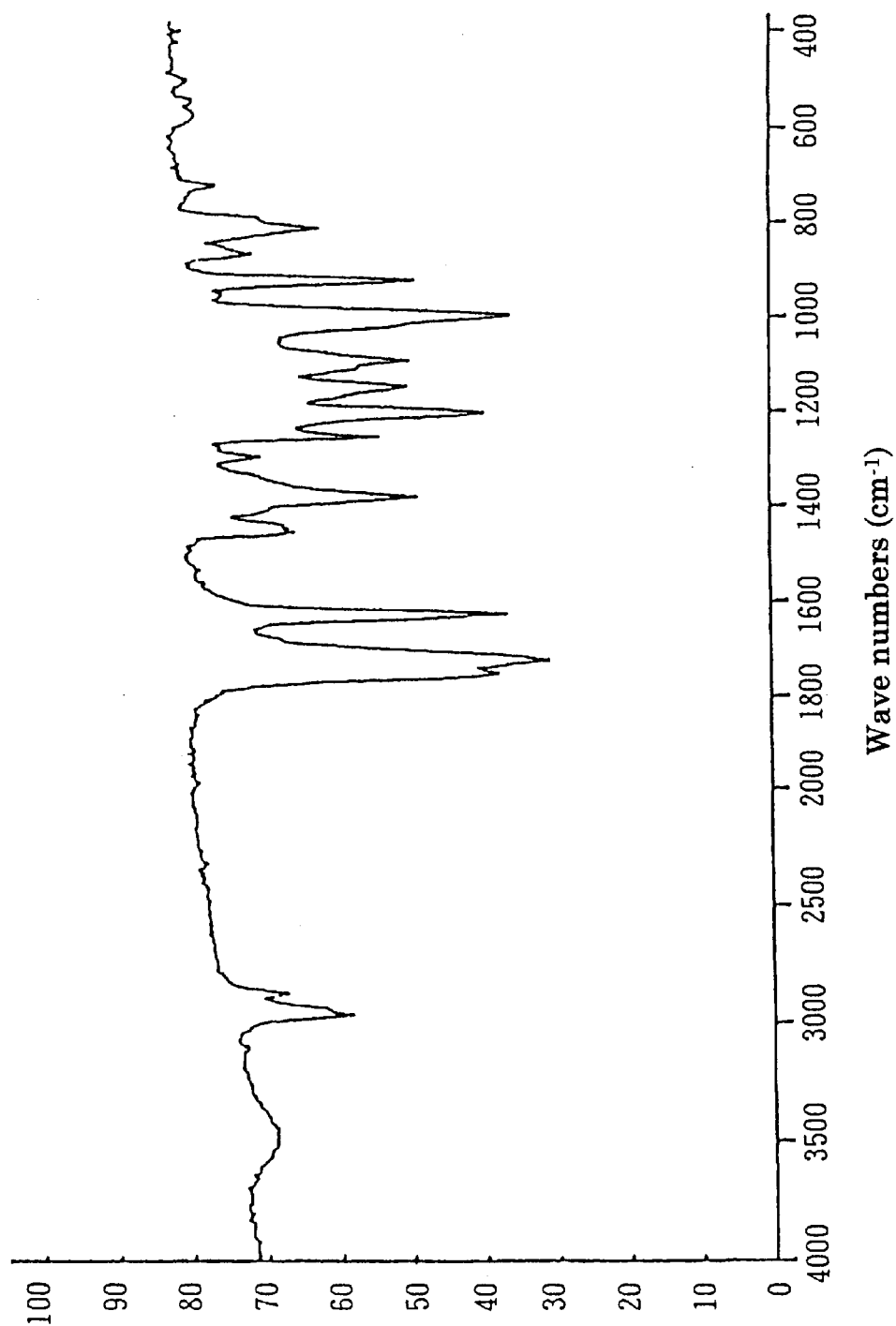
FIG. 2 is a chart showing the infrared absorption spectrum of the antibiotic TKR2648.

(5) IR spectrum (KBr method): the numbers of wave length (cm$^{-1}$) of major absorption are 2960, 1730, 1630, 1390, 1210, 1010, 930 as shown in FIG. 2.

(6) Solubility: Soluble in chloroform and methanol, sparingly soluble in hexane and water.

Figure 3:
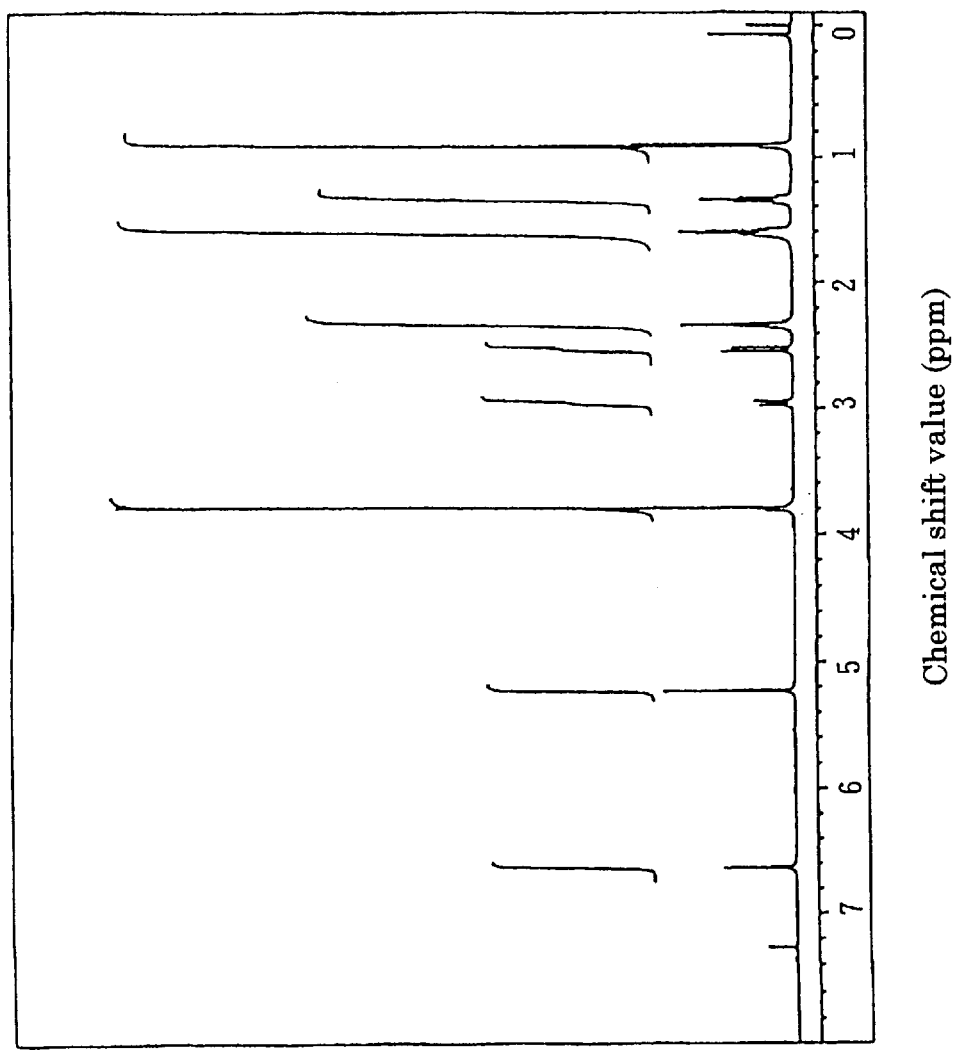
FIG. 3 is a chart showing the $^1$H-NMR spectrum of the antibiotic TKR2648.
Figure 4:
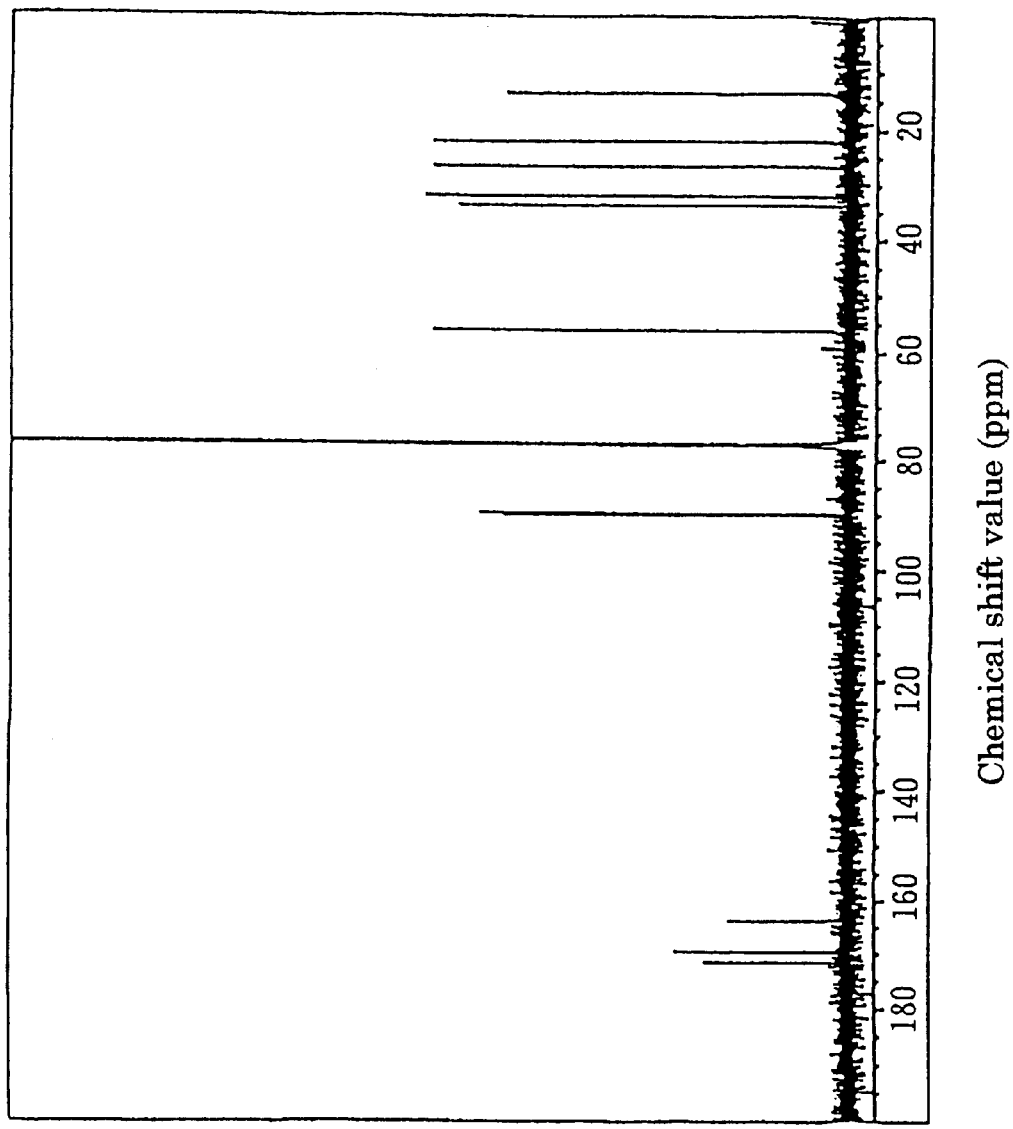
FIG. 4 is a chart showing the $^{13}$C-NMR spectrum of the antibiotic TKR2648.
Figure 5:
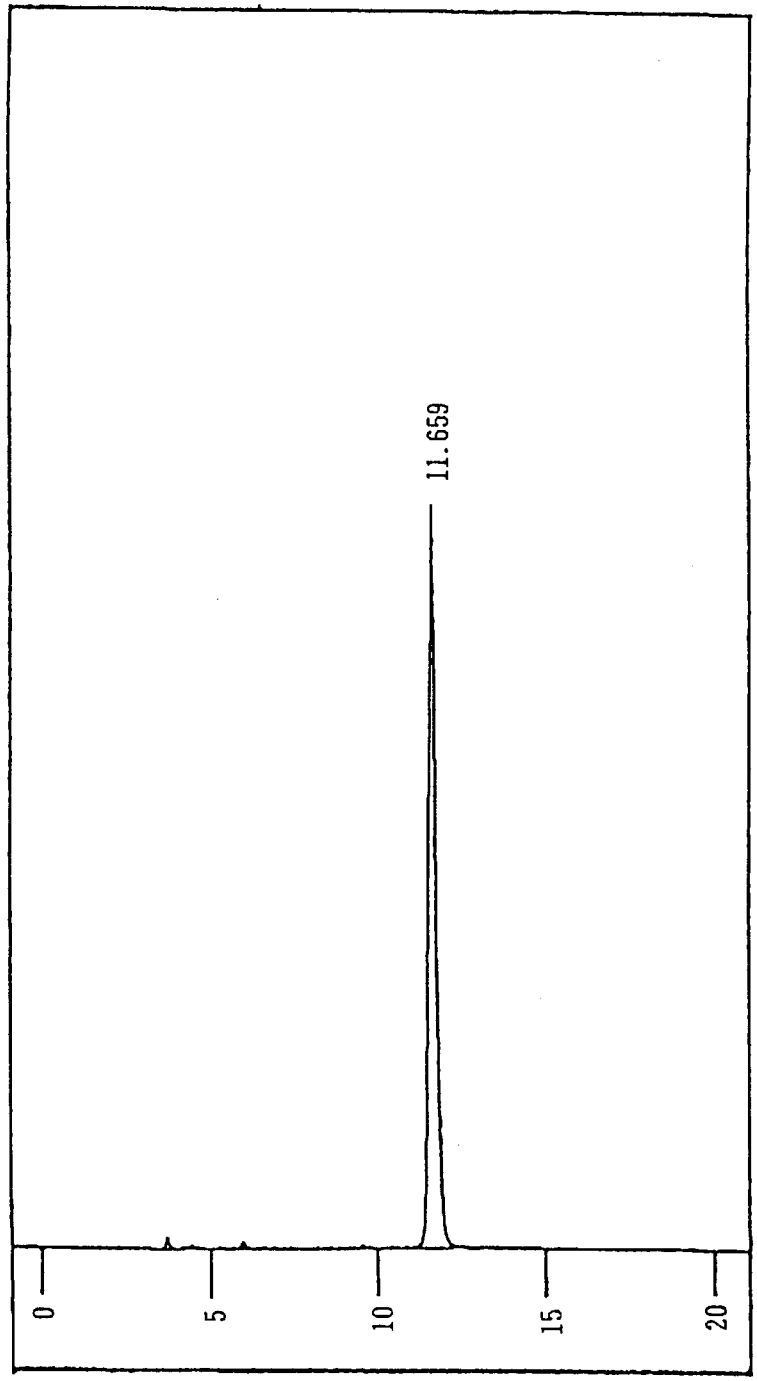
FIG. 5 is a HPLC chart of the antibiotic TKR2648 showing its elution position.

Furthermore, TKR2648 mentioned above has the $^1$H-NMR spectrum shown in FIG. 3 and the $^{13}$C-NMR spectrum shown in FIG. 4, and is characterized in that, in reversed-phase high-performance liquid chromatography, it is eluted in the position indicated in FIG. 5.

Furthermore, the abscissa represents wave length (nm) in FIG. 1. The abscissa represents wave numbers (cm$^{-1}$) in FIG. 2. The abscissa represents chemical shift value (ppm) in FIG. 3 and FIG. 4. The ordinate represents the relative intensity of ultraviolet absorption and the abscissa represents retention time (min.) in FIG. 5.

The above-mentioned TKR2648 can be produced by growing a strain of microorganism belonging to the genus Penicillium and capable of producing said TKR2648 in a culture medium and isolating the substance from the resulting culture broth.

There is no limitation on the strain of microorganism that can be used in the present invention only provided it belongs to the genus Penicillium and is capable of producing said TKR2648. Thus, for example, strain Penicillium sp. TKR2648 (hereinafter referred to as the TKR2648 strain) can be mentioned.

The above-mentioned TKR2648-strain is a novel strain not heretofore described in the literature, and isolated and characterized for the first time by the inventors of the present invention. The strain has the property to produce TKR2648 with advantage. The mycological characteristics of this TKR2648-strain are now described in detail.

The colonial colors of said TKR2648-strain on various media are shown in Table 1. The descriptions of colors in the table are based on those prescribed in Japanese Industrial Standard (JIS) Z8102 (1985) and reflect the results of observation on day 7 of culture at 25° C. after inoculation in the respective media.

TABLE 1

| Medium | Colony size diameter (mm) | Color of colony | Reverse color of the colony | Texture of the colony |
|---|---|---|---|---|
| Malt extract agar | 19 | Grayish yellow green 7.5GY5/2 | Dark green 10Y5/6 | Velvety |
| Potato dextrose agar | 24 | Grayish yellow green 5GY5/2 | Brownish green 5Y8/4 | Velvety |
| Czapek agar | 20 | Grayish green 10GY5/2 | Light grayish yellow green 10Y8/2 | Cottony |
| Sabouraud agar | 29 | Dark grayish yellow green 7.5GY4/2 | Light grayish yellow green 10Y8/2 | Velvety |
| YpSs agar | 25 | Grayish yellow green 5GY6/2 | Light grayish yellow 7.5Y8/2 | Cottony |

The above TKR2648-strain grows luxuriously on malt extract agar, potato dextrose agar, and Czapek agar etc., giving colonies showing a velvety surface texture and a slightly elevated center. The conidiophore of the TKR2648-strain measures 90 to 270×1.8 to 3.0 μm and has a glabrous surface, usually forming symmetrically bivertillate penicilli. The metula measures 12.0 to 14.0×2.8 to 3.2 μm, occurring in groups of 2 to 4, and the phialides are whorled and sized 9.0 to 10.0×1.8 to 2.4 μm. The conidia are globose to subglobose, each having a glabrous surface and measuring 2.2 to 3.2×2.4 to 4.0 μm.

Among the mycological characters of the TKR2648-strain, its physiological characteristics are as follows.

Temperature range for growth: The temperature range for growth is 10 to 25° C. and the optimum range of temperature for growth is about 20° C.

The pH range for growth: The pH range for growth is pH 3 to 9 and the optimum range of pH for growth is about pH 5.

When the above mycological characters are compared with the descriptions of Penicillium species in Carlos Ramirez, Manual and Atlas of the Penicillia, Elsevier Biomedical Press, 1982, and other literatures, the TKR2648 strain can be identified to be a strain belonging to the genus Penicillium.

However, no report was available on a strain of microorganism having the ability to produce TKR2648 among fungi of the genus Penicillium. Therefore, the inventors of the present invention regarded it as a novel strain and named Penicillium sp. TKR2648. The strain was deposited at National Institute of Bioscience and Human-Technology, Agency of Industrial Science and Technology (Address, 1-3, Higashi 1-chome, Tsukuba-shi, Ibaraki, Japan (Zip code 305)) under the accession number of FERM BP-6093 (original date of deposit: Oct. 8, 1996; date of request for transfer to international deposit: Sep. 2, 1997).

The present invention can be carried into practice not only with the above-mentioned TKR2648-strain but also with any spontaneous or artificial mutant of said TKR2648-strain or any other strain of microorganism belonging to the genus Penicillium and capable of producing TKR2648.

In accordance with the present invention, TKR2648 is produced by cultivating a TKR2648-producing strain in a nutrient medium. Nutrients to be used for the medium include various carbon sources such as glucose, fructose, saccharose, starch, dextrin, glycerol, molasses, malt syrup, oils and fats, and organic acids.

Nitrogen sources as nutrients include organic and inorganic nitrogenous substances such as soybean meal, cotton seed meal, corn steep liquor, casein, peptone, yeast extract, meat extract, wheat germs, urea, amino acids, ammonium salts, etc. Salts as nutrients are various inorganic salts such as salts of sodium, potassium, calcium, magnesium, etc. and salts of phosphoric acid. Those substances can be used independently or in a suitable combination.

Where necessary, the nutrient medium may be supplemented with heavy metal salts such as iron salts, copper salts, zinc salts, cobalt salts, etc., vitamins such as biotin, vitamin $B_1$, etc., and other organic and inorganic substances which would assist in growth of the microorganism and promote production of TKR2648.

In addition to the above components, an antifoamer and/or a surfactant, for example silicone oil, polyalkylene glycol ethers, etc., can be added to the nutrient medium.

In cultivating a strain of microorganism capable of producing TKR2648 in said nutrient medium, a variety of cultural methods which are generally used in the production of antibiotics by means of microorganisms can be employed. However, liquid culture, particularly shake culture or submerged aerobic culture, is preferred.

The cultivation is preferably carried out at 15 to 25° C. The pH of the medium may range from pH 3 to 8 but is preferably around pH 5. Regarding the incubation time, generally a sufficient output of the antibiotic can be expected by 3 to 8 days of culture.

By the above cultivation, TKR2648 is contained both intracellularly and extracellularly and accumulated in the culture broth. In the present invention, the TKR2648 accumulated in the culture broth can be recovered and isolated from the broth by utilizing its physicochemical characteristics and, where necessary, by further purification.

The above-mentioned recovery can be achieved by extracting the whole broth with a non-hydrophilic organic solvent such as ethyl acetate, butyl acetate, chloroform, butanol, methyl isobutyl ketone, or the like. As an alternative, it is possible to subject the broth to centrifugation or filtration to separate into the medium and cells and isolate the antibiotics from each of the medium and cells.

The TKR2648 can be separated from the medium not only by the above-mentioned extraction method using a non-hydrophilic organic solvent but also by the method which comprises contacting the medium with an adsorbent to let TKR2648 adsorbed on the adsorbent and desorbing or eluting them with a solvent. The adsorbent that can be used includes, for example, activated carbon, cellulose powder, and adsorbent resins. As the above-mentioned solvent, a variety of solvents can be selectively used according to the kind and properties of the adsorbent and either singly or in combination. Thus, an aqueous solution of one or more water-soluble organic solvents, such as aqueous acetone, aqueous alcohol, etc., can be employed. For separation of TKR2648 from the microorganisms, the extraction technique using a hydrophilic organic solvent such as acetone can be employed.

In the present invention, the crude extract of TKR2648 can be purified by the conventional techniques for the separation purified of hydrophobic antibiotics, e.g. by column chromatography or high-performance liquid chromatography, using a column packed with a stationary phase such as silica gel, activated alumina, activated charcoal, adsorbent resin, etc. The eluent that can be used for silica gel column chromatography includes chloroform, ethyl acetate, methanol, acetone, water, mixtures thereof, etc.

The resin for high-performance liquid chromatography includes chemically-derivatized silica gel, such as silica gel derivatives having octadecyl, octyl, or phenyl groups, and polystirenic porous polymer gels, while the mobile phase that can be used includes aqueous solutions of water-soluble organic solvents, such as aqueous methanol, aqueous acetonitrile, etc.

TKR2648 can each be put to use as such or in the form of a pharmacologically acceptable salt in medicinal applications. There is no particular limitation on the type of pharmacologically acceptable salt. Thus, the salt includes salts of mineral acids such as hydrochloric acid, sulfuric acid, nitric acid, phosphoric acid, hydrofluoric acid, hydrobromic acid, etc., salts of organic acids such as formic acid, acetic acid, tartaric acid, lactic acid, citric acid, fumaric acid, maleic acid, succinic acid, methanesulfonic acid, ethanesulfonic acid, benzenesulfonic acid, toluenesulfonic acid, naphthalenesulfonic acid, camphorsulfonic acid, etc., and salts of alkali metals or alkaline earth metals, such as sodium, potassium, calcium, etc.

To administer TKR2648 or its pharmacologically acceptable salt, as a drug, they can be administered either as such or in the form of a pharmaceutical composition containing typically 0.1 to 99.5%, preferably 0.5 to 90% thereof in a pharmaceutically acceptable, non toxic and inert carrier to animals inclusive of humans.

The carrier mentioned above includes solid, semisolid or liquid diluents, fillers, other formulation auxiliaries, etc. and such carriers can be used alone or in combination.

The above-mentioned pharmaceutical composition is preferably administered in unit dosage forms and can be administered orally, parenterally, topically (e.g. transdermally) or rectally. Of course, those pharmaceutical compositions should be administered in dosage forms suited for the respective route of administration.

For administration of TKR2648, or its pharmacologically acceptable salt, as a drug, the dose as an antifungal agent is preferably selected with reference to patient factors such as age and body weight, route of administration, nature and severity of disease, etc. Usually in man, however, the daily dose of the active ingredient for an adult patient is 10 to 2000 mg.

While a daily dose lower than the above range may be sufficient in some cases, a dose higher than the range may be required in other cases. When a high dose is used, the daily dosage is preferably administered in several divided doses.

The oral administration can be made using solid, powdery, or liquid dosage forms such as powders, diluted powders, tablets, dragees, capsules, drops, sublingual tablets, etc.

For the parenteral administration, liquid unit dosage forms for subcutaneous, intramuscular, or intravenous administration, typically solutions and suspensions, can be employed. These preparations can be manufactured by suspending or dissolving a predetermined amount of TKR2648, or a pharmaceutically acceptable salt thereof, in a nontoxic liquid carrier suitable for injection, such as an aqueous medium or an oily medium, and sterilizing the resulting suspension or solution.

The topical administration (e.g. transdermal administration) can be carried out using a variety of topical dosage forms such as liquids, creams, powders, pastes, gels, and ointments. These dosage forms can be manufactured by using a predetermined amount of TKR2648 or a pharmacologically acceptable salt thereof, in combination with one or more of the perfume, coloring agent, filler, surfactant, humectant, emollient, gelatinizer, carrier, preservative, stabilizer, etc., suitable for topical dosage formulations.

The rectal administration can be made using, for example, suppositories each mixing a predetermined amount of TKR2648, or its pharmacologically acceptable salt, with a low-melting solid base such as higher esters, e.g. myristyl palmitate, polyethylene glycol, cacao butter, or a mixture of them.

Best Mode of Carrying Out the Invention

The following examples are further illustrative of the present invention, but by no means limitative of the scope of the invention.

EXAMPLE 1

A loopful of TKR2648-strain (FERM BP-6093) from a slant culture was used to inoculate into a 500-ml Erlenmeyer flask containing 100 ml of liquid medium (Difco potato dextrose broth, 2.4% (w/v) ) and incubated on a shaker at 25° C. for 2 days to prepare a seed culture. This seed culture 1.0 ml was transferred to 20 Erlenmeyer flasks of 500 ml capacity each containing 125 ml of the same liquid medium as above and incubated (under shaking at 220 rpm) at 25° C. for 5 days. The obtained culture broth was centrifuged and the supernatant was separated from cells.

To the supernatant, ethyl acetate (3 L) was added. After sufficient mixing, the extract with ethyl acetate was concentrated under reduced pressure to recover 505 mg of a residue.

The residue thus obtained was dissolved in 0.8 ml of methanol and subjected to high-performance liquid chromatography to provide 84 mg of crude TKR2648. The high-performance liquid chromatography was carried out under the following conditions.

Apparatus: LC6A (manufactured by Shimadzu)

Column: YMC pack C18 (2.0 cm×25 cm) (manufactured by YMC)

Mobile phase: 25 to 100% (v/v) of methanol/water

The crude TKR2648 was dissolved in 0.8 ml of methanol and subjected to a column (150 ml) of Sephadex LH-20 (manufactured by Pharmacia) equilibrated with methanol. The column was eluted with methanol to isolate an active fraction. This fraction was concentrated under reduced pressure to provide 43 mg of residue.

The residue was dissolved in 0.4 ml of methanol and subjected to high-performance liquid chromatography to isolate an active fraction. This fraction was concentrated under reduced pressure to provide 3.2 mg of pure TKR2648 as white powder. This second high-performance liquid chromatography was carried out under the following conditions.

Apparatus: LC6A (manufactured by Shimadzu)

Column: YMC pack C18 (2.0 cm×25 cm) (manufactured by YMC)

Mobile phase: 36% (v/v) acetonitrile/water

Physicochemical Properties

Mass spectrometry was carried out by JMS-DX302 mass spectrometer (manufactured by Jeol Ltd.). $^1$H-NMR (in deuterated chloroform with tetramethylsilane as reference) and $^{13}$C-NMR (in deuterated chloroform with deuterated chloroform as reference) were performed by JNM-A500 nuclear magnetic resonance spectrometer (Jeol Ltd.). Specific optical rotation (in methanol) was determined by DIP370 digital polarimeter (manufactured by Jasco Ltd.). Ultraviolet spectrophotometry (in methanol) was carried out by UV-250 self-recording spectrophotometer (manufactured by Shimadzu), and infrared absorption spectrometry (KBr method) was by 270-30 infrared spectrophotometer (manufactured by Hitachi). Physicochemical properties of the substance TKR2648 were described below.

(1) Mass spectrometry

The purified white powdery product available upon vacuum concentration of the active fraction in said second high-performance liquid chromatography was found by FAB-MS to be a substance with a peak at m/z 229 [M+H]$^+$.

(2) Molecular formula

The purified white powdery product available upon vacuum concentration of the active fraction in said second high-performance liquid chromatography was found by high resolution FAB-MS to be a substance with a peak at m/z 229.1090 [M+H]$^+$. This result, and the $^1$H-NMR and $^{13}$C-NMR analyses showed that the purified compound had molecular formula of $C_{11}H_{16}O_5$ (caluculated value 229.1076).

The $^1$H-NMR spectrum and $^{13}$C-NMR spectrum of this product are presented in FIG. 3 and FIG. 4, respectively.

(3) Specific optical rotation

The specific optical rotation in methanol of the purified white powdery product available upon vacuum concentration of the active fraction in said second high-performance liquid chromatography was found to be as follows.

Specific optical rotation: $[\alpha]_D^{20}$+1260 (c 1.0, methanol)

(4) Ultraviolet absorption spectrum

The UV absorption in methanol of the purified white powdery product available upon vacuum concentration of the active fraction in the second high-performance liquid chromatography was found to be as follows.

UV (nm) ($E_{1cm}^{1\%}$): 232 (510)

The UV absorption spectrum is shown in FIG. 1.

(5) Infrared absorption spectrum

The IR spectrophotometric characterization (KBr method) of the purified white powdery product available upon vacuum concentration of the active fraction in the second high-performance liquid chromatography revealed the following numbers of wave length of major absorption.

IR (KBr) (cm$^{-1}$): 2960, 1730, 1630, 1390, 1210, 1010, 930

The IR absorption spectrum is shown in FIG. 2.

(6) Solubility

The above powder was soluble in chloroform and methanol, but practically insoluble in hexane and water.

Based on the above analyses, the purified white powdery product available upon vacuum concentration of the active fraction in the second high-performance liquid chromatography was identified to be TKR2648 and the purified white powdery product available upon vacuum concentration of the active fraction in the second high-performance liquid chromatography was identified to be TKR2648.

The above TKR2648 were analyzed by reversed-phase partition high-performance liquid chromatography (HPLC) using LC-10A high-performance liquid chromatography (manufactured by Shimadzu) This HPLC analysis was carried out under the following conditions.

Column: CAPCELLPAK $C_{18}$ (6 mm×150 mm) (manufactured by Shiseido)

Mobile phase: 0.05% trifluoroacetic acid-containing 40% (v/v) acetonitrile/water Column temperature: 40° C.

Detection UV wave length: 220 nm

As a result, the above TKR2648 was eluted in the position indicated in FIG. 5.

Biological characteristics (1) Antifungal Activity

The antifungal spectra of the above TKR2648 against various microorganisms were determined. Using the liquid medium dilution method, the concentration causing a substantially complete inhibition of fungal growth was determined as minimal inhibitory concentration ($\mu$g/ml). The results are presented in Table 2. In the table, YNBG stands for a medium comprising 0.67% of yeast nitrogen base (manufactured by Difco) and 1.0% of glucose, and BHI stands for a medium comprising 0.5% of brain-heart infusion bouillon (manufactured by Nihon Pharmaceutical).

TABLE 2

| Test strain | Medium | Minimal inhibitory concentration ($\mu$g/ml) |
|---|---|---|
| Candida albicans TIMM0136 | YNBG | 100 |
| Candida kefyr TIMM0301 | YNBG | 50 |
| Cryptococcus neoformans TIMM0354 | YNBG | 3.13 |
| Aspergillus fumigatus TIMM1776 | BHI | 6.25 |

It is apparent from Table 2 that TKR2648, the antibiotic according to the present invention, was active against pathogenic fungi such as Candida albicans, Candida kefyr, Cryptococcus neoformans, Asperaillus fumigatus etc.

(2) Inhibitory Activity of Tumor Metastasis

Effect of the above TKR2648 on tumor cells was examined by measuring inhibitory activity of the metastatic ability of tumor cells, which were inoculated into animals after incubation with TKR2648 for several hours.

EL-4 lymphoma or B16 melanoma cells were cultured in RPMI 1640 medium containing 10% of fetal calf serum, and various concentrations of TKR2648 were added to the culture of tumor cells. After overnight culture, cytotoxicity of TKR2648 to the cells was determined by alamarblue-method (Biosource International), and the cells treated with TKR2648 were recovered and injected to C57BL/6 (female) mice via tail vein. Ten days after the injection of EL-4, the mice were sacrified and their livers were obtained and weighed to determine metastasizing tumor cells as increase of weight. Fourteen days after the injection of B16 cells, the mice were scarified and their lungs were obtained and counted metastasizing melanoma colonies. The results are presented in Table 3. It is apparent from Table 3 that TKR2648 inhibited metastasis of EL-4 and B16 tumor cells to normal tissues at the concentrations showing little cytotoxicity. This means that TKR2648 may be useful as an anticancer agent by inhibiting metastasis properties of tumor cells without affecting of proliferative properties of tumor cells.

TABLE 3

| | | | EL4 | |
|---|---|---|---|---|
| Concentration (μg/ml) | Animals | Cytotoxicity (%) | Increase of liver weight mean ± SD (g) | Inhibition of metastasis (%) |
| 0 | 6 | 0 | 1.199 ± 0.078 | 0 |
| 0.156 | 3 | 4.5 | 0.630 ± 0.107* | 47.4 |
| 0.313 | 3 | 15.7 | 0.391 ± 0.148* | 67.4 |
| 0.625 | 3 | 35.1 | 0.128 ± 0.043* | 89.3 |
| 2.5 | 3 | | nt | |

| | | | B16 | |
|---|---|---|---|---|
| Concentration (μg/ml) | Animals | Cytotoxicity (%) | Colony number of melanoma mean ± SD (g) | Inhibition of metastasis (%) |
| 0 | 4 | 0 | 64.5 ± 14.8 | 0 |
| 0.156 | 3 | 4.5 | 58.3 ± 16.3 | 9.6 |
| 0.313 | 3 | | nt | |
| 0.625 | 3 | 14.1 | 45.3 ± 3.8 | 29.7 |
| 2.5 | 3 | 51.3 | 2.3 ± 2.3* | 96.4 |

Asterisks (*) mean significant differences at risk of p<0.001.

(3) Toxicity

Intraperitoneal administration of the TKR2648 obtained above at a dose of 50 mg/kg to ICR mice caused no toxic signs.

Merits of the Invention

As described above, the present invention provides the antifungal substances TKR2648 which are of use in clinical medicine, for example in the therapy of fungal infectious diseases or cancer, and a method for production of the substance.

What is claimed is:

1. Antibiotic TKR2648 having the structure I,

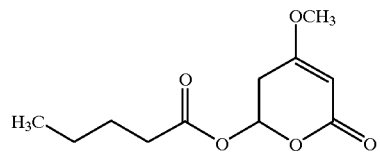

(I)

or a pharmaceutically acceptable salt thereof.

2. A process for preparing antibiotic TKR2648 having the structure I,

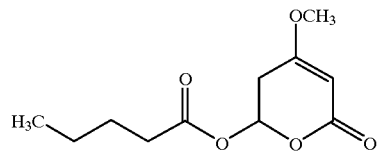

(I)

comprising culturing strain Penicillium TKR2648, FERM BP-6093, or a mutant thereof which produces antibiotic TKR2648, in an aqueous nutrient medium containing assimilable sources of carbon, nitrogen and inorganic substances, and recovering the compound of structure I.

3. A biologically pure culture of strain Penicillium TKR2648, FERM BP-6093, or a mutant thereof which produces antibiotic TKR2648 in a recoverable amount in an aqueous nutrient medium containing assimilable sources of carbon, nitrogen and inorganic substances.

* * * * *